US00PP37494P2

(12) United States Plant Patent
Branahagen

(10) Patent No.: US PP37,494 P2
(45) Date of Patent: Jun. 30, 2026

(54) ***CORNUS* TREE NAMED 'PGCFPP'**

(50) Latin Name: *Cornus florida*
Varietal Denomination: PGCFPP

(71) Applicant: Spring Meadow Nursery Inc, Grand Haven, MI (US)

(72) Inventor: Alan Branahagen, Rockford, IL (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/245,274

(22) Filed: Jun. 21, 2025

(51) Int. Cl.
*A01H 5/02* (2018.01)
*A01H 5/12* (2018.01)
*A01H 6/00* (2018.01)

(52) U.S. Cl.
USPC ..... Plt./220
CPC ..... *A01H 6/00* (2018.05); *A01H 5/02* (2013.01); *A01H 5/12* (2013.01)

(58) Field of Classification Search
USPC ..... Plt./220
CPC ..... A01H 5/02; A01H 5/00; A01H 6/00
See application file for complete search history.

*Primary Examiner* — June Hwu

(57) ABSTRACT

A new and distinct cultivar of *Cornus* tree named 'PGCFPP' is disclosed, characterized by large flower bracts that emerge greyed-red with a yellow-green base and mature to creamy white-yellow with a soft greyed-red blush which is strongest towards the apex. Trees are highly floriferous and produce vibrant, dark red autumn foliage. Overall canopy shape of the tree is broadly pyramidal. The new cultivar is a *Cornus*, used for ornamental landscape purposes.

4 Drawing Sheets

Latin name of the genus and species: *Cornus florida*.
Cultivar denomination: 'PGCFPP'.

BACKGROUND OF THE INVENTION

The new *Cornus* cultivar is a product of a planned breeding program conducted by the inventor to develop cultivars with new bract colors and heavy flowering. The new cultivar is the result of the open pollination of the seed parent, *Cornus florida* 'Cherokee Chief', unpatented. The pollen parent is unknown. The open pollination was conducted at a nursery in Kingsville, Missouri in 1997. *Cornus* 'PGCFPP' was found and selected by the inventor at the same nursery in Kingsville, Missouri in 2008.

Asexual reproduction of the new cultivar was performed by bud grafting. This was first performed at a nursery in Belvidere, Tennessee in 2013, and has shown that the unique features of this cultivar are stable and reproduced true to type in multiple successive generations.

Plants of the new cultivar were first disclosed to third parties Jun. 25, 2024, in the United States. Plants were shown at an invitational event in Grand Haven, MI. This disclosure was made directly by the inventor or one who obtained the claimed invention directly or indirectly from the inventor. This and all public disclosures made between Jun. 25, 2024, and the filing of this application fall within the exception allowed under 102(b)(1).

SUMMARY OF THE INVENTION

The cultivar 'PGCFPP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PGCFPP' These characteristics in combination distinguish 'PGCFPP' as a new and distinct *Cornus* cultivar:

1. Large flower bracts that emerge greyed-red with a yellow-green base and mature to creamy white-yellow with a soft greyed-red blush which is strongest towards the apex.
2. High floriferousness.
3. Broadly pyramidal overall canopy shape.
4. Vibrant bronze/burgundy fall foliage color.

PARENT COMPARISON

Plants of the new cultivar *Cornus* 'PGCFPP' are similar to plants of the seed parent in most horticultural characteristics; however, plants of the new cultivar 'PGCFPP' differ in the following:

1. Mature flower bract color of the new cultivar is creamy white-yellow with a soft greyed-red blush which is strongest towards the apex, while the flower bract color of the seed parent is red-pink.
2. Plants of the new cultivar are larger and taller at maturity than plants of the seed parent.

COMMERCIAL COMPARISON

Plants of the new cultivar 'PGCFPP' are comparable to the commercial cultivar *Cornus florida* 'Rubra', unpatented. The two *Cornus* cultivars are similar in most horticultural characteristics, however, the new cultivar 'PGCFPP' differs in the following:

1. Flower bract color of the new cultivar is creamy white-yellow with a soft greyed-red blush which is strongest towards the apex, while the flower bract color of this comparator is peach to red-pink.

2. Plant habit of the new cultivar is more upright and elliptic to globose, while the plant habit of this comparator is more spreading and broadly pyramidal.

BRIEF DESCRIPTION OF THE PHOTOGRAPHS

The accompanying photographs illustrate in full color various distinguishing characteristic of the new cultivar, 'PGCFPP' grown outdoors in Grand Haven, Michigan. The photographs were taken using conventional techniques and although colors may appear different from actual colors due to light reflectance it is as accurate as possible by conventional photographic techniques.

DETAILED BOTANICAL DESCRIPTION

Figure 1:
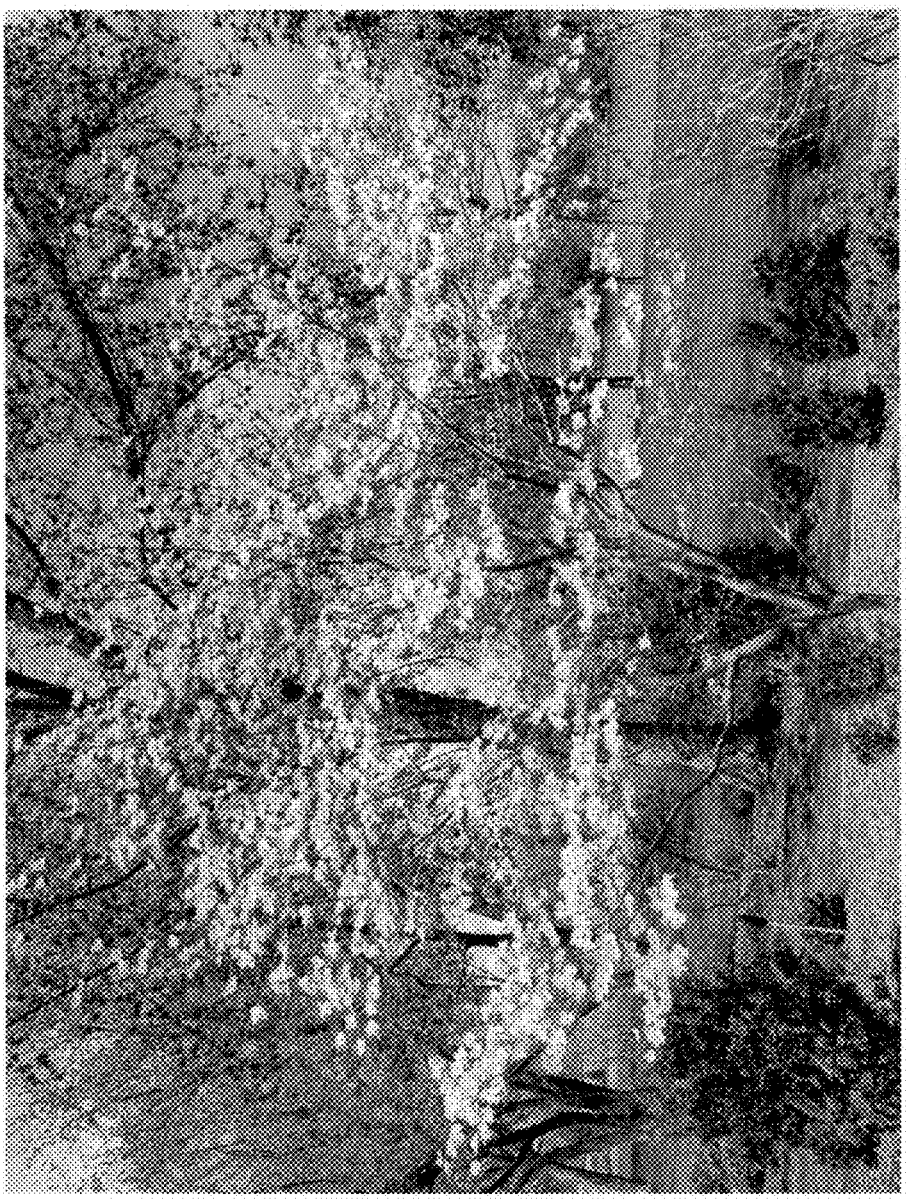
FIG. 1 illustrates a flowering tree of approximately 10 years in the ground in Kingsville, Missouri.
Figure 2:
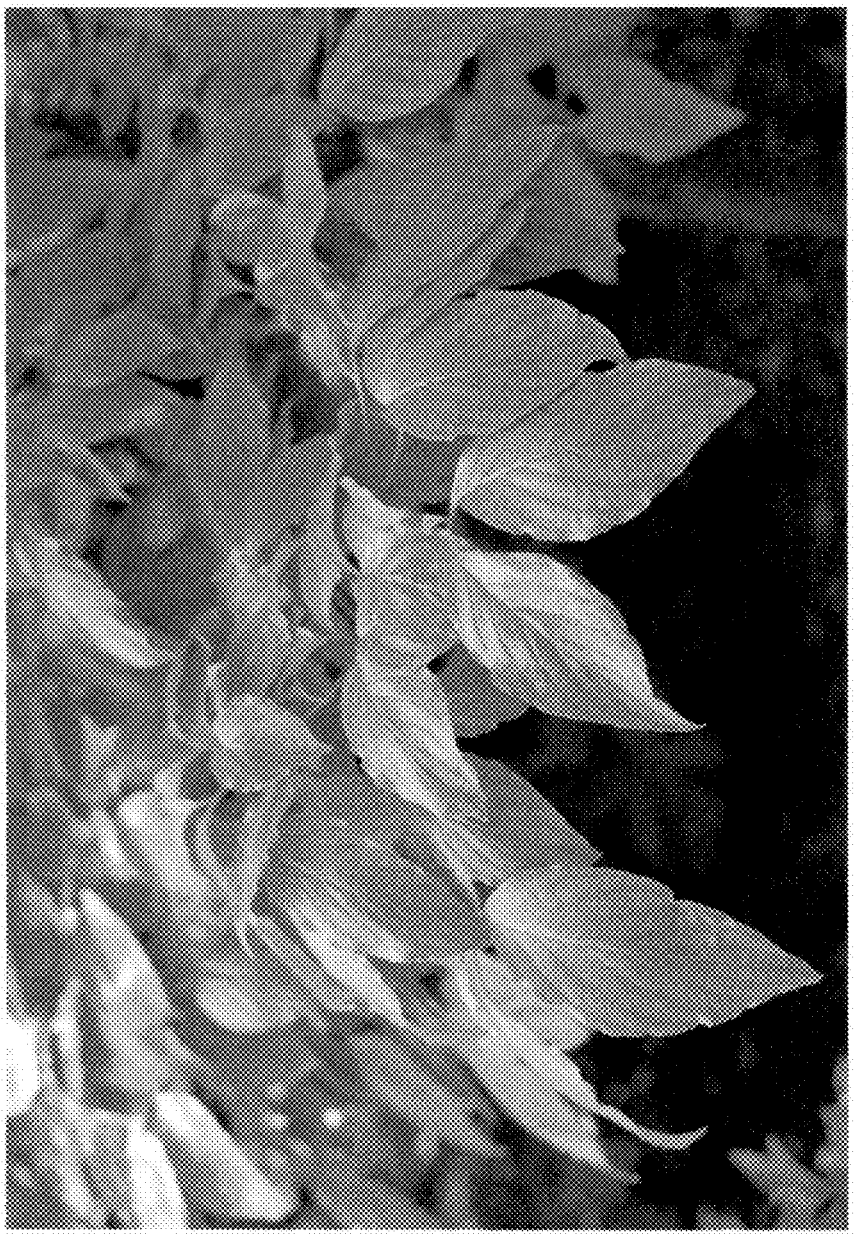
FIG. 2 illustrates a close-up view of the summer foliage.
Figure 3:
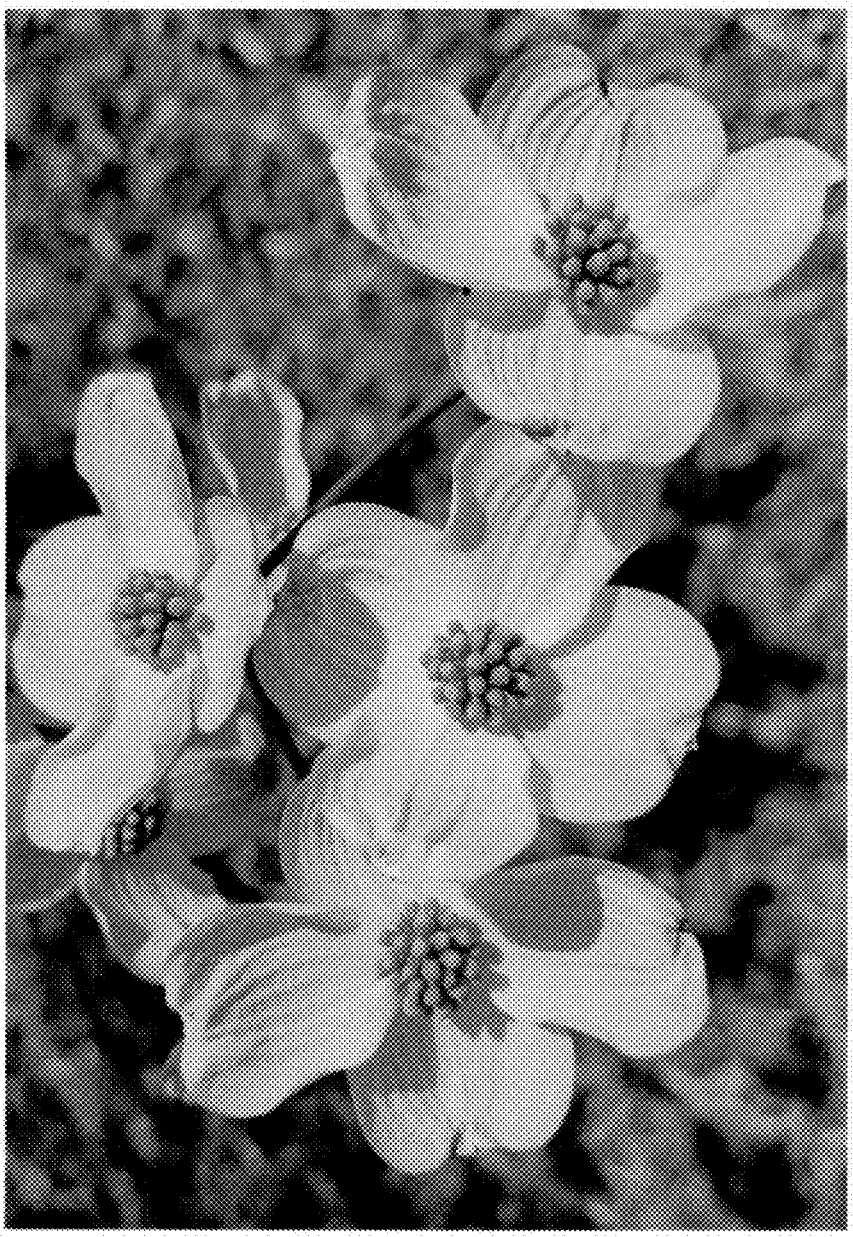
FIG. 3 illustrates a close-up view of the flowers
Figure 4:
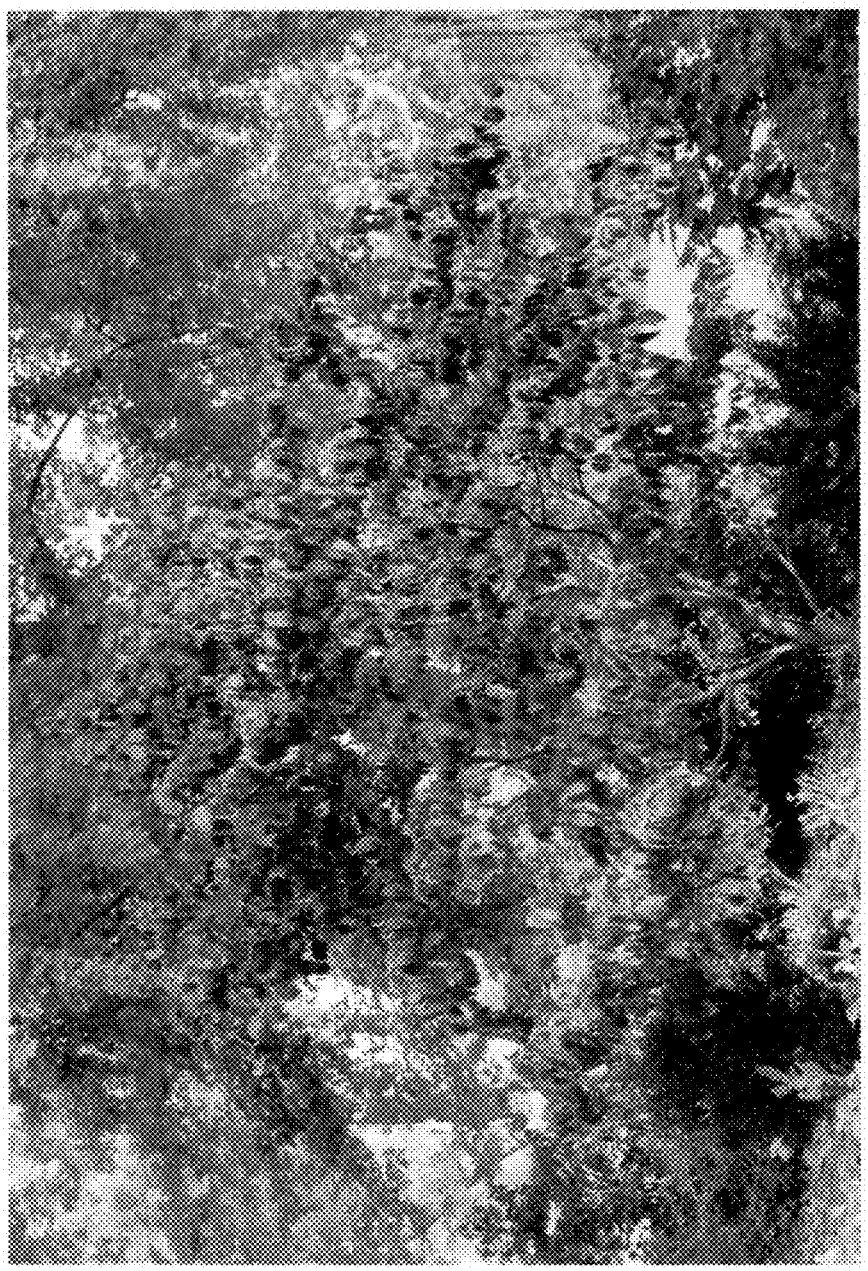
FIG. 4 illustrates a tree of approximately 10 years in the ground in Kingsville, Missouri in the fall, with foliage having turned its typical fall color.

In the following description, color references are made to The Royal Horticultural Society Colour Chart 6$^{th}$ Edition 2015 except where general terms of ordinary dictionary significance are used. The following observations and measurements describe 'PGCFPP' plants grown outdoors in Grand Haven, Michigan. The growing temperature ranged from approximately 8° C. to 32° C. during the day and from approximately 1° C. to 12° C. during the night. General light conditions are normal sunlight and numerical values represent averages of typical plant types.

Botanical classification: *Cornus florida* 'PGCFPP'.

PROPAGATION

Type of propagation typically used: Grafting.

PLANT

Age of plant described: 10 years.
Plant type: Flowering tree.
Growth habit: Spreading.
Plant spread: 4.5 m.
Plant height: 3.5 to 4.5 m.
Typical mature height: 3.5 to 5.5 m.
Typical mature spread: 4.5 m.
Overall plant shape: Broadly pyramidal.
Trunk:
- *Color*.—RHS Brown N200C.
- *Diameter*.—8 cm at breast height.
- *Texture*.—Scaly.

Branching characteristics:
Lateral branches:
- *Quantity*.—Approximately 10 to 12.
- *Diameter*.—Approximately 3 to 4 cm.
- *Length*.—Approximately 3 m.
- *Texture*.—Some scaled bark but smoother than trunk.
- *Color*.—RHS Brown N200C.
- *Aspect and Angle*.—Slightly undulating, occurring at an approximately 0° to 45° angle from stem.
- *Strength*.—High.
- *Branches occur how far apart*.—Approximately 40 to 60 cm.

FOLIAGE

Leaf:
- *Arrangement*.—Opposite.
- *Length*.—Approximately 12 cm.
- *Width*.—Approximately 6 cm.
- *Shape of blade*.—Elliptic to ovate.
- *Apex*.—Acuminate.
- *Base*.—Cuneate to oblique.
- *Attachment*.—Normal.
- *Margin*.—Entire.
- *Texture of top surface*.—Lightly pubescent.
- *Texture of bottom surface*.—Lightly pubescent.
- *Leaf internode length*.—10 cm.
- *Color*.—Young foliage upper side: RHS Yellow-Green 146C. Young foliage under side: RHS Yellow-Green 146D. Mature foliage upper side: RHS Yellow-Green 146C. Mature foliage under side: RHS Yellow-Green 146D. Fall color: Between RHS Greyed-Red 178A and Greyed-Purple 183A.
- *Venation*.—Type: Pinnate. Venation color upper side: RHS Yellow-Green 146C. Venation color under side: RHS Yellow-Green 146D.
- *Petiole*.—Length: 1 cm. Width: 2 mm. Color: RHS Yellow-Green 144A. Texture: Lightly pubescent.

FLOWER

Natural flowering season: Spring-April to May.
Inflorescence type and habit: Small, clustered flowers surrounded by showy, petal-like bracts.
Flower longevity on plant: Bracts persist for several weeks; flowers approximately 1 week.
Quantity of inflorescences: Approximately 200 inflorescences per lateral branch.
Quantity of flowers: Approximately 20 to 30 flowers per inflorescence.
Inflorescence size:
- *Including bracts*.—
  - *Diameter*.—Approximately 6.5 cm.
  - *Length*.—Approximately 6.5 cm.
- *Excluding bracts*.—
  - *Diameter*.—Approximately 1.2 cm.
  - *Length*.—Approximately 1.2 cm.

Peduncle:
- *Length*.—2 cm.
- *Diameter*.—2 mm.
- *Color*.—RHS Yellow-Green 145A.

Pedicel:
- *Length*.—2 mm.
- *Diameter*.—1 mm.
- *Color*.—RHS Yellow-Green 145A

Bracts:
- *Arrangement*.—Cruciform.
- *Length*.—3 cm.
- *Width*.—3 cm.
- *Margin*.—Entire.
- *Apex*.—Obtuse.
- *Base*.—Rounded.
- *Quantity*.—4.
- *Texture*.—Glabrous, somewhat coriaceous upper and lower surfaces.

*Color*.—When opening: Upper surface: RHS Greyed-Red 181B at apex, becoming Yellow-Green 145B at base. Lower surface: RHS Greyed-Red 181B at apex, becoming Yellow-Green 145B at base. Fully opened: Upper surface: RHS Yellow-White 158A with a Greyed-Red 181D blush, especially at apex. Lower surface: RHS Yellow-White 158A with a Greyed-Red 181D blush, especially at apex.

Bud:

*Shape*.—Narrowly elliptic.
*Length*.—Approximately 5 mm.
*Diameter*.—Approximately 2 mm.
*Color*.—RHS Yellow-Green 145A.

Petals:

*Arrangement*.—Whorl; cruciform.
*Length*.—3 mm.
*Width*.—2 mm.
*Margin*.—Entire.
*Apex*.—Acute.
*Base*.—Fused.
*Quantity*.—4.
*Texture*.—Glabrous upper and lower surfaces.
*Color*.—When opening: Upper surface: RHS Yellow-Green 144B to 144C. Lower surface: RHS Yellow-Green 144B to 144C. Fully opened: Upper surface: RHS Yellow-Green 144B to 144C. Lower surface: RHS Yellow-Green 144B to 144C.

Sepals:

*Length*.—0.5 mm.
*Width*.—0.5 mm.
*Shape*.—Triangular.
*Color*.—Interior Surface: RHS Yellow-Green 145B. Exterior Surface: RHS Yellow-Green 145B.
*Texture*.—Glabrous upper and lower surfaces.

Fragrance: None.

REPRODUCTIVE ORGANS

Androecium:

*Stamens quantity*.—4.
*Anther shape*.—Oblong.
*Anther size*.—1 mm.
*Anther color*.—RHS Yellow-Green 144D.
*Pollen color*.—RHS Yellow 11D.
*Pollen quantity*.—Low to moderate.

Gynoecium:

*Number of pistils per flower*.—1.
*Pistil length*.—1 mm.
*Stigma shape*.—Oblong.
*Stigma color*.—RHS Yellow-Green 144C.
*Style color*.—RHS Yellow-Green 144C.
*Style length*.—Approximately 0.5 mm.
*Ovary color*.—RHS Yellow-Green 144B.

OTHER CHARACTERISTICS

Fruits and seeds: Not observed to date.

Disease/pest resistance: Neither resistance nor susceptibility to other normal diseases and pests of *Cornus* observed.

Temperature range: Tolerant to USDA zone 5 to 9. Excellent tolerance to wind and rain.

What is claimed is:

1. A new and distinct cultivar of *Cornus* tree named 'PGCFPP' as herein illustrated and described.

* * * * *